(12) United States Patent
Aggarwal et al.

(10) Patent No.: US 11,141,083 B2
(45) Date of Patent: Oct. 12, 2021

(54) SYSTEM AND METHOD FOR OBTAINING BLOOD GLUCOSE CONCENTRATION USING TEMPORAL INDEPENDENT COMPONENT ANALYSIS (ICA)

(71) Applicant: SAMSUNG ELECTRONICS CO., LTD., Suwon-si (KR)

(72) Inventors: Gorish Aggarwal, Karnataka (IN); Kiran Bynam, Karnataka (IN); Sujit Jos, Karnataka (IN); So Young Lee, Daejeon (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 352 days.

(21) Appl. No.: 16/183,325

(22) Filed: Nov. 7, 2018

(65) Prior Publication Data
US 2019/0159703 A1   May 30, 2019

(30) Foreign Application Priority Data

Nov. 29, 2017   (IN) .............................. 201741042881
Jun. 29, 2018   (KR) ........................ 10-2018-0075311

(51) Int. Cl.
| | |
|---|---|
| *A61B 5/1455* | (2006.01) |
| *A61B 5/145* | (2006.01) |
| *A61B 5/00* | (2006.01) |
| *G01N 33/49* | (2006.01) |
| *G06N 20/00* | (2019.01) |

(Continued)

(52) U.S. Cl.
CPC ........ *A61B 5/14532* (2013.01); *A61B 5/1455* (2013.01); *A61B 5/725* (2013.01); *A61B 5/7257* (2013.01); *A61B 5/7267* (2013.01); *G01N 33/49* (2013.01); *G06N 20/00* (2019.01); *G16H 50/20* (2018.01); *G16H 10/40* (2018.01)

(58) Field of Classification Search
CPC . A61B 5/1455; A61B 5/14532; A61B 5/7267; A61B 5/725; A61B 5/7257
See application file for complete search history.

(56) References Cited

U.S. PATENT DOCUMENTS

| | | | |
|---|---|---|---|
| 7,343,187 B2 | 3/2008 | Stetson | |
| 7,436,511 B2 | 10/2008 | Ruchti et al. | |

(Continued)

FOREIGN PATENT DOCUMENTS

| | | |
|---|---|---|
| JP | 2005245636 A | 9/2005 |
| JP | 2006280421 A | 10/2006 |

(Continued)

OTHER PUBLICATIONS

Communication dated Oct. 14, 2020 issued by Intellectual Property India in Indian Application No. 201741042881.

*Primary Examiner* — Eric F Winakur
(74) *Attorney, Agent, or Firm* — Sughrue Mion, PLLC

(57) ABSTRACT

A method for obtaining blood glucose concentration using near infrared spectroscopy (NIR) data is provided. The method includes obtaining, by an independent component analysis (ICA) temporal module, orthogonal pure spectra from human NIR spectra; performing, by a processing module, one or more preprocessings and drift removal on the human NIR spectra and the orthogonal pure spectra to obtain preprocessed spectra; and obtaining, by a regression block, the blood glucose concentration from the preprocessed spectra.

17 Claims, 3 Drawing Sheets

(51) Int. Cl.
    *G16H 50/20*    (2018.01)
    *G16H 10/40*    (2018.01)

(56) References Cited

U.S. PATENT DOCUMENTS

| | | |
|---|---|---|
| 7,613,488 B1 | 11/2009 | Maracas et al. |
| 8,019,399 B2 | 9/2011 | Kawasaki et al. |
| 2010/0324398 A1 * | 12/2010 | Tzyy-Ping ......... A61B 5/14532 600/365 |
| 2011/0200237 A1 | 8/2011 | Nakamura et al. |
| 2013/0204102 A1 | 8/2013 | Sen et al. |
| 2014/0303464 A1 | 10/2014 | Izzetoglu et al. |
| 2014/0372081 A1 | 12/2014 | Izzetoglu et al. |
| 2015/0025340 A1 | 1/2015 | Kanai et al. |
| 2015/0320319 A1 | 11/2015 | Alfano et al. |

FOREIGN PATENT DOCUMENTS

| | | |
|---|---|---|
| JP | 2015021833 A | 2/2015 |
| KR | 10-2002-0028406 A | 4/2002 |
| WO | 03/010510 A2 | 2/2003 |

\* cited by examiner

SYSTEM AND METHOD FOR OBTAINING BLOOD GLUCOSE CONCENTRATION USING TEMPORAL INDEPENDENT COMPONENT ANALYSIS (ICA)

CROSS-REFERENCE TO RELATED APPLICATION(S)

This application claims priority from Indian Patent Application No. 201741042881, filed on Nov. 29, 2017 in the Indian Intellectual Property Office, and Korean Patent Application No. 10-2018-0075311, filed on Jun. 29, 2018 in the Korean Intellectual Property Office, the disclosures of which are hereby incorporated in their entireties by reference.

BACKGROUND

1. Technical Field

Systems, devices, and methods consistent with exemplary embodiments relate to glucose monitoring, and more particularly relates to obtaining blood glucose concentration using temporal independent component analysis (ICA).

2. Description of the Related Art

Glucose monitoring is used for testing level of glucose concentration in blood, and can be performed either invasively or non-invasively. In the invasive method, skin of a person is pierced to obtain blood sample for testing, and in the non-invasive method, collection of blood sample is not required for obtaining the glucose concentration. Some of the typical methods used for non-invasive glucose monitoring include Mid Infrared (Mid IR), Near Infrared (NIR), and Raman spectroscopy. In recent years, the NIR method is commonly used for continuous glucose monitoring, in which the IR waves are made to pass through the skin and absorption of the IR waves by the subcutaneous portion of skin is used in determining the glucose level. The absorption of the wave by the sample is defined by BEER Lambert law:

$$A = \log\left(\frac{I}{I_0}\right) = \epsilon C d \quad (1)$$

Where E is absorption coefficient, C is concentration of component in sample and d is penetration depth.

If the sample is composed of different constituents having different coefficients ($\epsilon_1, \epsilon_2, \ldots \epsilon_n$) and concentrations ($C_1, C_2, \ldots C_n$), then overall absorption can be given as the following equation:

$$A = \epsilon_1 C_1 d + \epsilon_2 C_2 d + \ldots + \epsilon_n C_n d \quad (2)$$

The NIR spectrum of the skin is composed of absorption of the IR waves by several components such as water, fat (or cholesterol), protein (e.g., collagen and keratin), amino acids, elastin and glucose. Therefore, the NIR spectrum of the skin can be obtained as the following equation:

$$A_{NIR} = A_{Water} + A_{Cholesterol} + A_{Collagen} + A_{Keratin} + A_{Elastin} + A_{Acid} + A_{Glucose}$$

Monitoring of glucose concentration non-invasively is very challenging as the concentration of glucose in blood is several orders lesser than that of other constituents and many times, the glucose information is buried under the noise and drift components of the NIR spectra. The orders of concentration of different constituents are shown in the below table:

| Constituent | Water | Fat | Protein | Elastin/Acid | Glucose |
|---|---|---|---|---|---|
| Order of concentration(~) | $10^0$ | $10^{-1}$ | $10^{-3}$ | $10^{-3}$ | $10^{-4}$ |

Related art methods for monitoring glucose levels using an NIR spectrum includes a non-contact analysis method of solid samples in NIR Diffusion reflectance measurement, wherein Independent Component Analysis is performed on the mixed spectra to separate the mixed spectra into the pure analyte spectra and their concentration profiles. The related art method also uses a scatter correction to remove the non-linear effects from the measured spectra. However, the related art method does not address the issue of instrumental/environmental residual drift reducing SNR in an actual scenario. Further, the related art method uses independent component analysis (ICA) algorithm that assumes statistically independent source signals and non-zero kurtosis. However, in many of the cases, bio medical source signals are dependent on each other and have very low kurtosis value, which significantly degrades the accuracy in monitoring glucose levels.

Another related art method for monitoring glucose levels is based on an approach for analysis of Near Infrared (NIR) data using Independent Component Analysis (ICA), wherein a Blind Source Separation is performed on a non-analyte mixture to identify the concentration of individual mixture. The method uses a mixture made from starch, water and protein for experimentation. However, the ICA algorithm used in the related art method assumes interdependence of source signals and that the concentration of each components of the mixture is not time varying. However, for a human body, the concentration of components may change with time. Further, the related art method does not address the challenge of concentration of one component (e.g., glucose) being very low compared to that of other components (e.g., water and protein), which significantly degrades the accuracy of human skin NIR analysis.

Another related art method for monitoring glucose levels includes a method for measuring blood glucose using only the portion of the IR spectrum which contains the NIR water absorption peaks, wherein the related art method uses electromagnetic (EM) radiation of a wavelength transmitted through the skin to the measurement region, for example, a blood vessel. The collected light is analyzed and compared against a stored reference calibration curve to calculate blood glucose concentration. However, the related art method assumes that the background interference is common for an entire range of the near infrared region. Further, the related art method uses a reference calibration curve which varies from person to person and hence universality is not guaranteed. It is assumed in the related art method that all constituents of the human skin is known and well understood in the NIR spectrum. This is not true for the case of human skin. This will affect the accuracy in determination of the glucose level.

Therefore, there is a need for a method for identifying the pure spectra of various skin components directly from the NIR spectra. Further, there is a need for a method for modifying the original ICA algorithm to obtain representations of orthogonal pure spectra even if the actual pure spectra are dependent on each other. Further, there is a need for a method, in which the obtained spectra is used by the temporal ICA algorithm to obtain the glucose concentration in the NIR spectra without the need for in vitro pure spectra. Further, there is need for a method for obtaining blood glucose concentration using temporal independent component analysis (ICA).

SUMMARY

One or more exemplary embodiments provide a method for obtaining blood glucose concentration using temporal independent component analysis (ICA).

According to an aspect of an exemplary embodiment, there is provided a method for obtaining blood glucose concentration using near infrared spectroscopy (NIR) data, the method including: obtaining, by an independent component analysis (ICA) temporal module, orthogonal pure spectra from human NIR spectra; performing, by a processing module, one or more preprocessings and drift removal on the human NIR spectra and the orthogonal pure spectra to obtain preprocessed spectra; and obtaining, by a regression block, the blood glucose concentration from the preprocessed spectra.

The obtaining the orthogonal pure spectra may include: receiving, by a pre-data whitening unit, the human NIR spectra; obtaining, by the pre-data whitening unit, data whitened NIR spectra based on performing transformation on the human NIR spectra; calculating, by an iterative processing unit, an orthogonal pure spectrum from the data whitened NIR spectra; calculating new deflated NIR spectra to be transmitted to the iterative processing unit, to compute a new orthogonal pure spectrum based on removal of an effect of the previously calculated orthogonal pure spectrum; and combining one or more computed orthogonal pure spectrums to obtain the orthogonal pure spectra.

The obtaining the data whitened NIR spectra may include: calculating Eigen vectors of the human NIR spectra using a singular value decomposition; and applying a whitening transformation using the Eigen vectors on the human NIR spectra to obtain the data whitened NIR spectra.

The calculating the orthogonal pure spectrum may include: computing, by a single processing unit, an estimate spectrum, based on the data whitened NIR spectra and a residual error; and reiterating the computing of the estimate spectrum until convergence of learning parameters is achieved to obtain the orthogonal pure spectrum.

The computing the estimate spectrum may include: randomly initializing the learning parameters, the learning parameters including a weight vector and a bias vector; obtaining the estimate spectrum based on the weight vector and the bias vector; and computing source statistics for the estimate spectrum, the source statistics including Cross correlation and Covariance matrix.

The reiterating may include: calculating updated values of the weight vector and the bias vector based on the source statistics of the estimate spectrum; calculating an updated estimate spectrum based on the updated values of the weight vector and the bias vector; determining the updated estimate spectrum as the orthogonal pure spectrum in response to the convergence being achieved for the weight vector; and reiterating the computing of the estimate spectrum in response to the convergence not being achieved for the weight vector.

The calculating the new deflated NIR spectra may include: deflating the data whitened NIR spectra based on the orthogonal pure spectrum obtained from the iterative processing unit; determining whether a certain number of orthogonal pure spectrums are obtained; and transmitting the deflated NIR spectra to the iterative processing unit to obtain a new orthogonal pure spectrum in response to the certain number of the orthogonal pure spectrums are not obtained.

The obtaining the preprocessed spectra may include: performing an extended multiplicative scatter correction (EMSC) method on the human NIR spectra and the orthogonal pure spectra; performing, by using a Fast Fourier Transform (FFT) block, a filtering method to obtain filtered spectra; and performing, on the filtered spectra, drift removal to obtain the preprocessed spectra.

The obtaining the filtered spectra may include: subsequent to performing the EMSC method, performing a Fourier domain filtering on the human NIR spectra to reduce noise on the human NIR spectra by using a Hanning Window; and removing drift by differentiating, with respect to a wavelength, Fourier domain filtered spectra, to obtain the filtered spectra.

The obtaining the blood glucose concentration may include: extracting, by a feature extraction block, one or more features from the preprocessed spectra; obtaining a training data set and a validation data set from the one or more features; and obtaining the blood glucose concentration by performing regression on the training data set and the validation data set.

According to an aspect of another exemplary embodiment, there is provided a system for obtaining blood glucose concentration using near infrared spectroscopy (NIR) data, the system including: an independent component analysis (ICA) temporal module configured to obtain orthogonal pure spectra from human NIR spectra; a processing module configured to perform one or more preproces sings and drift removal on the human NIR spectra and the orthogonal pure spectra to obtain preprocessed spectra; and a regression block configured to obtain the blood glucose concentration from the preprocessed spectra.

The ICA temporal module may include: a pre-data whitening unit configured to: receive the human NIR spectra; and obtain data whitened NIR spectra based on performing transformation on the human NIR spectra; an iterative processing unit configured to calculate an orthogonal pure spectrum from the data whitened NIR spectra; a deflation module configured to calculate new deflated NIR spectra to be transmitted to the iterative processing unit, to compute a new orthogonal pure spectrum based on removal of an effect of the previously calculated orthogonal pure spectrum; and a learning algorithm unit configured to combine one or more computed orthogonal pure spectrums to obtain the orthogonal pure spectra.

The pre-data whitening unit may obtain Eigen vectors of the human NIR spectra using a singular value decomposition, and apply a whitening transformation using the Eigen vectors on the human NIR spectra to obtain the data whitened NIR spectra.

The learning algorithm unit may compute, by a single processing unit included in the learning algorithm unit, an estimate spectrum, based on the data whitened NIR spectra and a residual error.

The learning algorithm unit may compute the estimate spectrum by performing: randomly initializing learning parameters, the learning parameters including a weight vector and a bias vector; obtaining the estimate spectrum based on the weight vector and the bias vector; and computing a source statistics for the estimate spectrum, the source statistics including Cross correlation and Covariance matrix; and reiterating computing of the estimate spectrum until convergence of the learning parameters is achieved to obtain the orthogonal pure spectrum.

The reiterating may include: calculating updated values of the weight vector and the bias vector based on the source statistics of the estimate spectrum; calculating an updated estimate spectrum based on the updated values of the weight vector and the bias vector; determining the updated estimate spectrum as the orthogonal pure spectrum in response to the convergence being achieved for the weight vector; and reiterating the updated values of the weight vector and the bias vector to the single processing unit in response to the convergence not being achieved for the weight vector.

The deflation module may deflate the data whitened NIR spectra based on the orthogonal pure spectrum obtained from the iterative processing unit; determine whether a certain number of orthogonal pure spectrums are obtained, and transmit the deflated NIR spectra to the iterative processing unit to obtain a new orthogonal pure spectrum in response to the certain number of the orthogonal pure spectrums not being obtained.

The processing module may include: an extended multiplicative scatter correction (EMSC) module configured to perform an extended multiplicative scatter correction (EMSC) method on the human NIR spectra and the orthogonal pure spectra; a Fast Fourier Transform (FFT) block configured to perform a filtering method to obtain filtered spectra; and a drift removal module configured to perform drift removal on the filtered spectra to obtain the preprocessed spectra.

The regression block may include: a feature extraction block configured to extract one or more features from the preprocessed spectra; a separation block configured to obtain a training data set and a validation data set from the one or more features; and a regression model identifier block configured to obtain the blood glucose concentration based on performing regression on the training data set and the validation data set.

BRIEF DESCRIPTION OF THE DRAWINGS

The above and/or other aspects will become apparent and more readily appreciated by describing certain exemplary embodiments with reference to the accompanying drawings in which.

DETAILED DESCRIPTION

Figure 1:
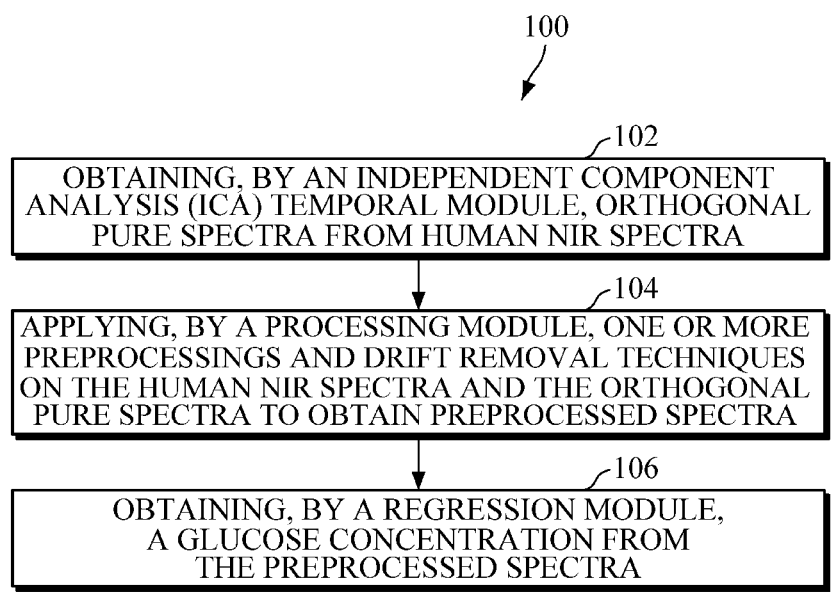
FIG. 1 illustrates a schematic flow diagram illustrating a method for obtaining blood glucose concentration using temporal independent component analysis (ICA), according to an exemplary embodiment.

In the following detailed description, exemplary embodiments will be described with reference to the accompanying drawings. Descriptions of well-known components and processing techniques are omitted so as to not unnecessarily obscure the embodiments herein. The examples used herein are intended merely to facilitate an understanding of ways in which the embodiments herein can be practiced and to further enable those of skill in the art to practice the embodiments herein. Accordingly, the examples should not be construed as limiting the scope of the embodiments herein. It should be understood that other embodiments may be utilized and that changes may be made without departing from the scope of the disclosure. The following detailed description is, therefore, not to be taken in a limiting sense, and the scope of the disclosure is defined only by the appended claims.

The specification may refer to "an", "one" or "some" embodiment(s) in several locations. This does not necessarily imply that each such reference is to the same embodiment(s), or that the feature only applies to a single embodiment. Single features of different embodiments may also be combined to provide other embodiments.

As used herein, the singular forms "a", "an" and "the" are intended to include the plural forms as well, unless expressly stated otherwise. It will be further understood that the terms "includes", "comprises", "including" and/or "comprising" when used in this specification, specify the presence of stated features, integers, s, operations, elements and/or components, but do not preclude the presence or addition of one or more other features, integers, steps, operations, elements, components, and/or groups thereof. As used herein, the term "and/or" includes any and all combinations and arrangements of one or more of the associated listed items.

Unless otherwise defined, all terms (including technical and scientific terms) used herein have the same meaning as commonly understood by one of ordinary skill in the art to which this disclosure pertains. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The disclosure describes a method for obtaining blood glucose concentration using temporal independent component analysis (ICA). According to an exemplary embodiment, the method comprises an Independent Component Analysis (ICA) temporal module to obtain an orthogonal pure spectrum from human Near Infrared Spectroscopy (NIR) spectra. The human NIR spectra are received and provided to the ICA temporal module to be used to obtain the orthogonal pure spectra with respect to the human NIR spectra.

In an exemplary embodiment, obtaining the orthogonal pure spectrum comprises receiving, by a pre-data whitening unit, human NIR spectra. The pre-data whitening unit provides data whitened NIR spectra after applying a transformation on the human NIR spectra. In another exemplary embodiment, obtaining the data whitened NIR spectra comprises calculating Eigen vectors of the input NIR spectra using singular value decomposition method. Further, a whitening transformation is applied using the Eigen vectors on the input NIR spectra to obtain the data whitened NIR spectra.

Further, obtaining the orthogonal pure spectra comprises calculating, by an iterative processing unit, an orthogonal pure spectrum from the data whitened NIR spectra. In another exemplary embodiment, the method for obtaining blood glucose concentration comprises calculating the orthogonal pure spectra, which comprises computing an estimate spectrum by a single processing unit, based on the data whitened NIR spectra and a residual error, while computing the estimate spectrum. The computing an estimate spectrum by the single processing unit comprises randomly initializing the learning parameters, which comprises a weight vector and a bias vector, obtaining an estimate spectrum based on the weight vector and the bias vector, and computing source statistics for the estimate spectrum, the source statistics comprising a Cross correlation and Covariance matrix. Further, the method for obtaining blood glucose concentration comprises combining all computed orthogonal pure spectrum to obtain an orthogonal pure spectra.

Further, calculating individual orthogonal pure spectra comprises reiterating over the estimate spectrum until convergence of learning parameters is achieved to obtain an orthogonal pure spectrum, wherein the reiterating over the estimate spectrum to obtain the orthogonal pure spectrum comprises calculating updated values of the weight vector and the bias vector based on the source statistics of the estimate spectrum, calculating the updated estimate spectrum based on the updated values of the weight vector and the bias vector, assigning the updated estimate spectrum values as the orthogonal pure spectrum in response to convergence being achieved for the weight vector, and reiterating the above operations in response to convergence not being reached.

Further, the method of obtaining a pure spectrum comprises calculating new deflated NIR spectra to be transmitted back to the iterative processing unit, to compute a new orthogonal pure spectrum, after removing the effect of the orthogonal pure spectrum previously calculated. In an exemplary embodiment, calculating the new deflated NIR spectra to be transmitted back to the iterative processing unit comprises deflating the data whitened NIR spectra based on the orthogonal pure spectrum obtained from the iterative processing unit. Further, the method for obtaining blood glucose concentration comprises checking if a certain number of the orthogonal pure spectrums are obtained. Further, the method for obtaining blood glucose concentration comprises sending back the deflated NIR spectra to the iterative processing unit to obtain a new orthogonal pure spectrum if the certain number of the orthogonal pure spectrums are not obtained.

Further, the method for obtaining blood glucose concentration is based on a processing module applying one or more preproces sings and drift removal techniques on the human NIR spectra and the orthogonal pure spectra to obtain a preprocessed spectra. The ICA temporal module filters the human NIR spectra and obtains the orthogonal pure spectra. The orthogonal pure spectra along with the human NIR spectra are transmitted to the processing module that receives the orthogonal pure spectra and human NIR spectra, and applies one or more processing and drift removal techniques to the human NIR spectra and the orthogonal pure spectra to obtain preprocessed spectra. Upon applying one or more preprocessings and drift removal techniques to the human NIR spectra and the orthogonal pure spectra components, the processing module obtains the preprocessed spectra.

In an exemplary embodiment, obtaining the preprocessed spectra comprises applying an extended multiplicative scatter correction (EMSC) method on the human NIR spectra and the orthogonal pure spectra. Further, the method for obtaining blood glucose concentration comprises applying, by means of a Fast Fourier Transform (FFT) block, filtering methods to obtain filtered spectra, wherein obtaining the filtered spectra comprises applying a Fourier domain filtering on the human NIR spectra after performing the EMSC method to reduce the impact of noise on the human NIR spectra by using a Hanning Window, and differentiating, with respect to a wavelength, the Fourier domain filtered spectra to remove the impact of drift, which is constant with respect to the wavelength to obtain the filtered spectra. Further, the method for obtaining blood glucose concentration comprises applying, on the filtered spectra, drift removal techniques to obtain the preprocessed spectra.

Further, the method for obtaining blood glucose concentration comprises a regression block obtaining a glucose concentration from the preprocessed spectra. The processing module transmits the preprocessed spectra to the regression block. The regression block receives the preprocessed spectra and provides the data to the feature extraction block, wherein the feature extraction block extracts one or more features from the obtained preprocessed spectra. Further, the method for obtaining blood glucose concentration comprises obtaining a training data set and a validation data set from the feature. Further, the method for obtaining blood glucose concentration comprises obtaining the glucose concentration upon performing regression on the training data set and the validation data set.

FIG. 1 illustrates a schematic flow diagram 100 illustrating a method for obtaining blood glucose concentration using temporal independent component analysis (ICA), according to an exemplary embodiment.

According to the flow diagram 100, at operation 102, an Independent Component Analysis (ICA) temporal module obtains orthogonal pure spectra from human NIR spectra. Further, at operation 104, a processing module applies one or more preprocessings and drift removal techniques on the human NIR spectra and the orthogonal pure spectra to obtain preprocessed spectra. Further, at operation 106, a regression block obtains a glucose concentration from the preprocessed spectra.

Figure 2:
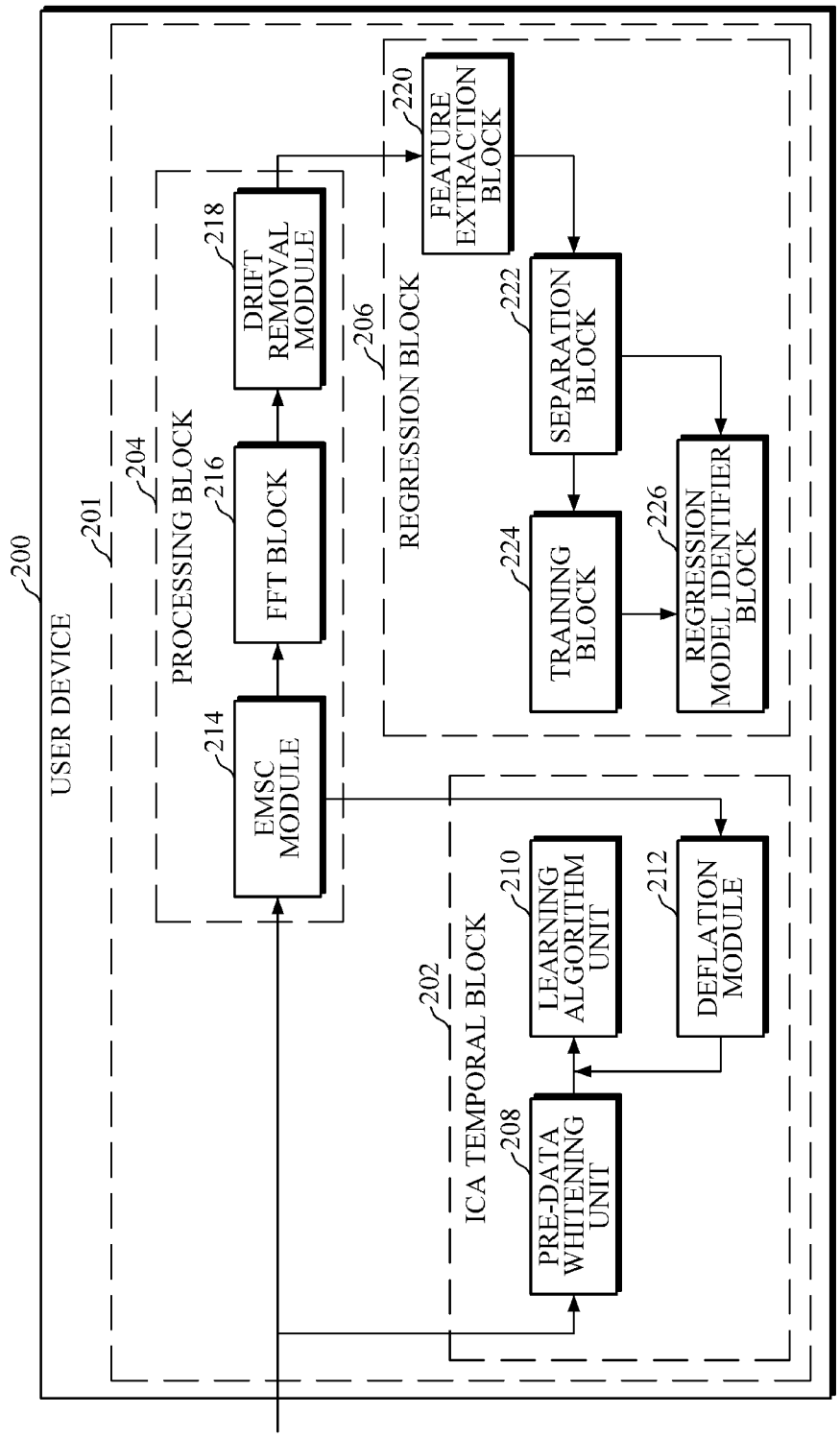
FIG. 2 is a schematic block diagram illustrating units for obtaining blood glucose concentration using temporal independent component analysis (ICA), according to an exemplary embodiment.

FIG. 2 is a schematic block diagram of a user device (or an apparatus for obtaining blood glucose concentration) 200 illustrating components for obtaining blood glucose concentration using temporal independent component analysis (ICA), according to an exemplary embodiment.

According to an exemplary embodiment shown in FIG. 2, the user device 200 includes at least one processor 201 including an independent component analysis (ICA) temporal block 202, a processing block 204, and a regression block 206. Further, the ICA temporal block 202 comprises a pre-data whitening unit 208, a learning algorithm unit 210, and a deflation module 212. Further, the processing block 204 comprises an extended multiplicative scatter correction (EMSC) module 214, a Fast Fourier Transform (FFT) block 216, and a drift removal module 218. Further, the regression block 206 comprises a feature extraction block 220, a separation block 222, a training block 224, and a regression model identifier block 226. According to an exemplary embodiment, Independent Component Analysis (ICA) is a method used to separate multivariate signal into additive components. The ICA defines a generative model for the observed multivariate data, which is typically given as a large database of samples. The ICA is a case of Blind Source Separation, wherein the ICA is a statistical and computational technique for revealing hidden factors that underlie sets of random variables, measurements, or signals.

Consider an example, in which a random data vector $x=(x_1, x_2, \ldots x_m)^T$ is given as a weighted sum of independent components $s_p$, $p=1, \ldots n$, such that $$x = \Sigma_p a_p * s_p \qquad (3)$$

where $a_p$ are mixing weights.

The ICA is used to transform observed data x, using linear transformation W into maximally independent components y as $$y = W * x \qquad (4)$$

Conventional ICA techniques are based on a principle of assuming non Gaussianity and statistical independence of source signals. The requirement of assuming non Gaussianity and statistical independence of source signals does not permit its use to many real life scenarios where the source signals (y) are commonly dependent on each other. In non-invasive continuous glucose monitoring (CGM), the pure spectra of components in skin such as, but not limited to, glucose, water, fat, collagen, keratin, acid, and the like have a high correlation. Further, a mean normalized spectrum extracted for one or more components is not capable of appropriately capturing the peaks of the pure spectra of components. Thus, the peaks of the pure spectra of components cannot be extracted from NIR spectra through conventional ICA techniques.

The ICA temporal block 202 according to an exemplary embodiment overcomes the above discussed problem, wherein the ICA temporal block 202 works on a batch learning method for sequential blind source extraction. Further, the ICA temporal block 202 works on signals obtained from non-additive white (i.i.d.) temporally correlated sources. The ICA temporal block 202 comprises the pre-data whitening unit 208, the learning algorithm unit 210, and the deflation module 212.

The pre-data whitening unit 208 receives human NIR spectra. The pre-data whitening unit 208 further provides data whitened NIR spectra after removing error from the human NIR spectra. Further, the pre-data whitening unit 208 calculates Eigen vectors of the human NIR spectra using singular value decomposition method. Further, a whitening transformation is applied by the pre-data whitening unit 208 using the Eigen vectors of the human NIR spectra to find the data whitened NIR spectra.

Further, the pre-data whitening unit 208 provides the data whitened NIR spectra to the learning algorithm unit 210 that calculates, using an iterative processing unit, an orthogonal pure spectrum from the data whitened NIR spectra. The learning algorithm unit 210 comprises a single processing unit, wherein the learning algorithm unit 210 computes an estimate spectrum based on the data whitened NIR spectra and a residual error while computing the estimate spectrum, wherein computing the estimate spectra from the single processing unit comprises randomly initializing the learning parameters, the learning parameters comprising a weight vector and a bias vector. Further, the learning algorithm unit 210 obtains an estimate spectrum based on the weight vector and the bias vector, and computes source statistics for the estimate spectrum comprising a Cross correlation and Covariance matrix.

Further, the learning algorithm unit 210 of the ICA temporal block 202 reiterates, over the estimate spectrum, operations of the single processing unit, to obtain orthogonal pure spectra, wherein the reiterating comprises calculating updated values of the weight vector and the bias vector based on the source statistics of the estimate spectrum, calculating the updated estimate spectrum based on the updated values of the weight vector and the bias vector, assigning the updated estimate spectrum as the orthogonal pure spectrum in response to convergence being achieved for the weight vector, and reiterating the operations of the single processing unit in response to convergence not being achieved.

Further, the learning algorithm unit 210 provides the orthogonal pure spectrum value to the deflation module 212 that calculates new deflated NIR spectra to be sent back to the iterative processing unit after removing the effect of the orthogonal pure spectra. The deflation module 212 deflates the data whitened NIR spectra based on the orthogonal pure spectrum obtained from the iterative processing unit. Further, the deflation module 212 checks whether a certain number of orthogonal pure spectrum are obtained. Further, the deflation module 212 transmits back the deflated NIR spectra to the iterative processing unit to obtain a new orthogonal pure spectrum in response to the required number of orthogonal pure spectra not being obtained.

According to an exemplary embodiment, the ICA temporal block 202 does not assume statistical independence or non-zero kurtosis for the source signals (e.g., pure spectra), but only assumes different temporal structures for the pure spectra, which is true as they have different auto correlation. The ICA temporal block 202 uses a method based on second order statistics to compute orthogonal pure spectra, thus is computationally efficient than related art methods.

For instance, consider that the ICA temporal block 202 estimates each orthogonal pure spectrum from the human NIR spectra one at a time. Assume the human NIR spectra to be $x(k)=[x_1(k), x_2(k), \ldots x_m(k)]^T$ for each time instant k, wherein x can be represented as:

$$x(k)=As(k)+n(k) \quad (5)$$

where A is an m×n unknown mixing matrix or concentrations, s(k) is a vector of unknown pure spectra, and n(k) is an additive white (i.i.d.) noise vector.

In the equation (5), it is required to determine maximally independent components/orthogonal pure spectrum, y(k), which can optimally represent s(k).

<Operation of Pre Data Whitening>

Using the ICA temporal block method according to an exemplary embodiment, the human NIR spectra X is mean and standard deviation normalized to give $\bar{X}$, wherein $\bar{X}$ is transmitted to a pre-data whitening block to calculate eigen vectors of the human NIR spectra and apply the whitening transformation, to obtain data whitened NIR spectra. The eigen vectors E and D can be calculated using:

$$[E,D]=eig(\bar{X}'^*\bar{X})$$

The whitening transformation to obtain the data whitened NIR spectra $\tilde{X}$ is expressed in Equation (6).

$$\tilde{X}=ED^{1/2}E\cdot\bar{X} \quad (6)$$

Further, data whitening renders the covariance matrix of data whitened NIR spectra $R_{xx}$ to be equal to $I_n$:

$$R_{xx}=E(\tilde{X}'^*\tilde{X})=I_n \quad (7)$$

This helps to ensure that data whitened NIR spectra $\tilde{X}$ is orthogonal and their projections over each other are zero.

<Operation of Learning Block>

In the learning block, each spectrum is calculated through Blind extraction technique. Assume the Data whitened NIR spectra to be x(k) and the first spectra $y_1(k)$ need to be extracted. Then, a single processing unit is described as:

$$y_1(k)=w_1^T*x(k)=\Sigma_{j=1}^m w_{1j}x_j(k) \quad (8)$$

$$\varepsilon_1(k)=y_1(k)-\Sigma_p^L b_{1p}y_1(k-p)=w_1^T*x(k)-b_1^T\widetilde{y_1} \quad (9)$$

where $w_1=[w_{11},w_{12},\ldots,w_{1m}]^T$ $\widetilde{y_1}=[y_1(k-1),y_1(k-2),y_1(k-L)]^T$ $b_1=[b_{11},b_{12},b_{1L}]^T$ The outputs of the single processing unit $y_1(k)$ and $\varepsilon_1(k)$ represent the extracted spectra, and the error after passing $y_1(k)$ by an FIR filter $b_1$ respectively.

Figure 3:
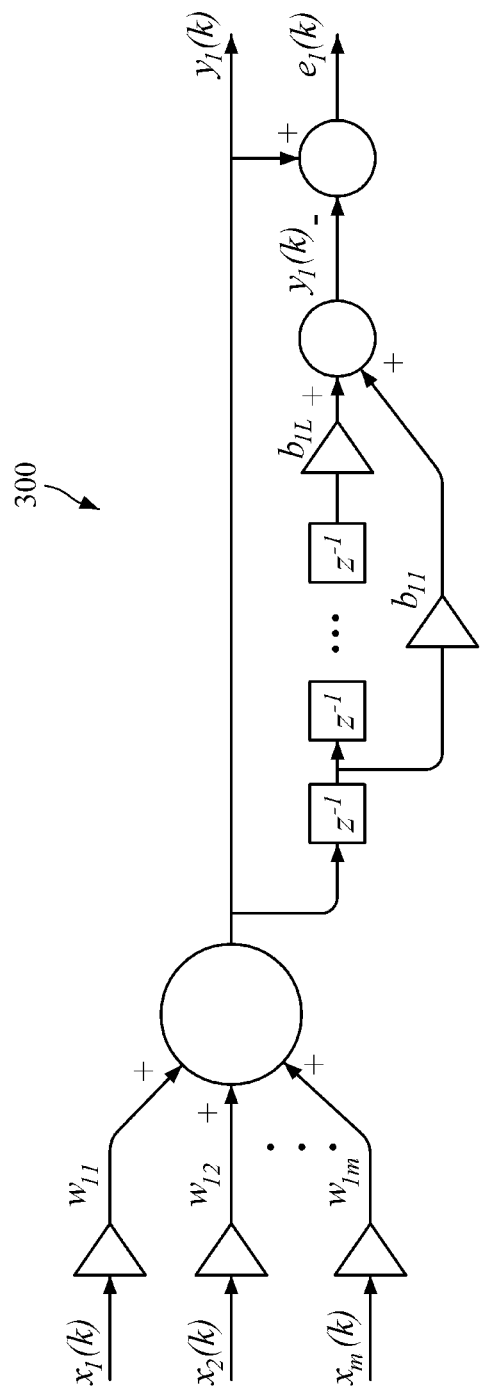
FIG. 3 is a schematic diagram illustrating single processing unit for extracting spectra, according to an exemplary embodiment.

FIG. 3 is a schematic diagram illustrating single processing unit 300 for extracting spectra, according to an exemplary embodiment.

According to an exemplary embodiment, the single processing unit 300 extracts one orthogonal pure spectrum from a plurality of orthogonal pure spectrums in the received data whitened NIR spectra. The single processing unit 300 estimates the optimal values of vectors $w_1$ and $b_1$ so as to extract spectra. Hence, a cost function $J(w_1, b_1)$ is defined as:

$$J(w_1, b_1) = E\{\varepsilon^2\} \quad (10)$$

From Equations 9 and 10, the result obtained can be defined as:

$$J(w_1, b_1) = w_1^T R_{xx} w_1 - 2 w_1^T R_{x\tilde{y}_1} b_1 + b_1^T R_{\tilde{y}_1 \tilde{y}_1} b_1 \quad (11)$$

where Covariance Matrix $R_{xx} = E\{xx^T\}$ and
Cross correlation Matrices $$R_{x\tilde{y}_1} = E\{x\tilde{y}_1^T\}, R_{\tilde{y}_1\tilde{y}_1} = E\{\tilde{y}_1\tilde{y}_1^T\}$$

Further, the learning algorithm unit of ICA temporal block 202 minimizes cost function $J(w_1, b_1)$ to estimate each orthogonal pure spectrum. By differentiating $J(w_1, b_1)$ with respect to $w_1$ and $b_1$ separately and equating them to 0, the result obtained would be:

$$w_1 = R_{xx}^{-1} R_{x\tilde{y}_1} b_1 \quad (12)$$

$$b_1 = R_{\tilde{y}_1\tilde{y}_1}^{-1} R_{\tilde{y}_1 x} w_1 = R_{\tilde{y}_1\tilde{y}_1}^{-1} R_{\tilde{y}_1 y_1} \quad (13)$$

Equations (12) and (13) together represent an iterative method, similar to an expectation-maximization (EM) method where the parameters of the previous iteration are used to learn new statistics. Also, from Equation (7), $R_{xx} = I_n$. Therefore, Equation (12) becomes:

$$w_1 = R_{x\tilde{y}_1} b_1 \quad (14)$$

Therefore, the operations of a single processing unit for ICA temporal can be summarized as:

1. Randomly initializing $w_1$ and $b_1$.
2. Obtaining $y_1$ using the current value of $w_1$ (Equation (8)).
3. Computing the statistics of source ($R_{xx}$, $R_{x\tilde{y}_1}$ and $R_{\tilde{y}_1\tilde{y}_1}$) keeping $w_1$ and $b_1$ constant.
4. Updating the learning parameters $w_1$ and $b_1$ using Equations (12) and (13).
5. In response to $w_1$ convergence being achieved, extracting current $y_1$ spectra.

Otherwise, above operations are repeated.

Further, the deflation module 212 deflates the input to remove the effect of orthogonal pure spectrum derived in a previous operation from data whitened NIR spectra using Equation (15):

$$x_{i+1}(k) = x_i(k) - \tilde{w}_i * y_i(k) \quad (15)$$

where $x_{i+1}(k)$ is the deflated NIR spectra.

Further, $\tilde{w}_i$ is calculated by minimizing mean square cost function $J_i(\tilde{w}_i) = E\{x_{i+1}^T x_{i+1}\}$ with respect to $\tilde{w}_i$, which will give:

$$\tilde{w}_i = \frac{E\{x_i y_i\}}{E\{y_i^2\}} = \frac{E\{x_i x_i^T\} w_i}{E\{y_i^2\}} \quad (16)$$

where $w_i$ is the learning parameter obtained from the last iterative operation. Since, by the pre-data whitening unit 208, the human NIR spectra were whitened to obtain data whitened spectra, Equation (16) can be simplified to:

$$\tilde{w}_i = w_i \quad (17)$$

The value of $\tilde{w}_i$ is fed back to the learning algorithm in an iterative fashion to derive the next orthogonal pure spectrum. The above operations are repeated till a certain number of orthogonal pure spectrums are obtained, wherein the orthogonal pure spectrum extracted is appropriately capable of capturing the peaks in all range of wavenumber, adequately representing the pure spectra.

Further, the processing block 204 of the user device 200 comprises the EMSC module 214, the Fast Fourier Transform (FFT) block 216, and the drift removal module 218. The processing block 204 applies one or more preprocessings and drift removal techniques on the orthogonal pure spectra components to obtain preprocessed spectra. The processing block 204 receives the human NIR spectra and orthogonal pure spectra from the ICA temporal block 202, and provides the data to the extended multiplicative scatter correction (EMSC) module 214. The EMSC module 214 applies an extended multiplicative scatter correction (EMSC) method on the human NIR spectra, uses the orthogonal pure spectra and regress for their compositions in the NIR spectra. For instance, let Y be any human NIR spectra comprising various pure spectra $X_1, X_2, \ldots, X_k$ for different blood components. Then, Y can be obtained using simple Linear Regression at any given wavelength as follows:

$$Y(n) = a_0 + \Sigma_{k=1}^M a_k X_k \quad (18)$$

where $a_k$ are the strengths of blood component and $a_0$ is a DC component.

Taking $X_1$ as the glucose spectra, the glucose spectra can be obtained by subtracting other components in the given spectra:

$$X_1 = Y - a_0 - \Sigma_{k=2}^M a_k X_k \quad (19)$$

The data can be further provided to the FFT block 216, wherein FFT filtering methods are applied to reduce impact of noise on the spectra and obtain filtered spectra. In the FFT filtering method, a Fourier domain filtering is performed on the human NIR spectra after EMSC is applied to reduce the impact of noise on the spectra by using a Hanning Window of size $N_{win}$, which is expressed in the following equations:

$$X(k) = \text{FFT}(x(n))$$

$$x_{fd}(t) = \text{IFFT}(X(k) * \text{Hanning}(N_{win}))$$

Further, the FFT block 216 comprises a differential block that acts as a supplement to the drift removal block to remove the impact of constant drift with respect to a wavelength. Mathematically, the differential block is denoted as $$\frac{d(X(k))}{d\lambda}.$$

With respect to a wavelength, the differential block differentiates the Fourier domain filtered spectra to remove the impact of drift, which is constant with respect to a wavelength, to obtain filtered spectra. Based on the filtered spectra obtained from the FFT block and the differential block, a correlation value for each feature index with respect to glucose without and with the FFT filtering and the differentiation by the differential block can be obtained.

From the comparison, it can be observed that there is an increase in the correlation for the most of the indices after the FFT filtering and the differentiation.

Further, the data from the FFT block 216 can be provided to the drift removal module 218 that applies a drift removal method to obtain the preprocessed spectra by removing the effect of experimental/instrumental drift in the NIR spectra. During drift removal method, it is assumed that NIR spectra contain only linear drift.

Further, the user device 200 comprises the regression block 206 that performs regression on the processed data and calculates glucose output from the processed data. The regression block 206 comprises the feature extraction block 220, the separation block 222, the training block 224, and the regression model identifier block 226. The feature extraction block 220 receives the spectra obtained after data processing block as input and extracts one or more features associated with the processed data signal. The features are the wavelength spectrums which show consistent high correlations with the glucose concentration. The obtained features are provided to the separation block 222 that separates training data set and validation data set.

The training data set is further provided to the training block 224 that receives the training data set and trains the regression model. In an exemplary embodiment, the training block 224 uses a principal components regression (PCR) method for training the data set. This is merely an example and the disclosure is not limited thereto. The person having ordinarily skill in the art can use any of other similar known methods of regression for training the regression model, without departing from the scope of the invention. Further, the regression model identifier block 226 receives the trained data set from the training block 224 and validation data set from the separation block 222, and obtains the glucose concentration upon performing regression on the training data set and the validation data set.

At least one of the components, elements or units represented by a block in the drawings may be embodied as various numbers of hardware, software and/or firmware structures that execute respective functions described above, according to an exemplary embodiment. For example, at least one of these components, elements or units may use a direct circuit structure, such as a memory, processing, logic, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions. Also, at least one of these components, elements or units may further include a processor such as a central processing unit (CPU) that performs the respective functions, a microprocessor, or the like. Further, although a bus is not illustrated in the above block diagrams, communication between the components, elements or units may be performed through the bus. Functional aspects of the above exemplary embodiments may be implemented in algorithms that execute on one or more processors. Furthermore, the components, elements or units represented by a block or processing steps may employ any number of related art techniques for electronics configuration, signal processing and/or control, data processing and the like.

The "unit" or "module" used herein may be a hardware component, such as a processor or a circuit, and/or a software component that is executed by a hardware component such as a processor.

Although a few embodiments have been shown and described, it would be appreciated by those skilled in the art that changes may be made in the exemplary embodiments without departing from the principles and spirit of the disclosure, the scope of which is defined in the claims and their equivalents.

What is claimed:

1. A method for obtaining blood glucose concentration using near infrared spectroscopy (NIR) data, the method comprising:
    obtaining, by an independent component analysis (ICA) temporal module, orthogonal pure spectra from human NIR spectra;
    performing, by a processing module, one or more pre-processings and drift removal on the human NIR spectra and the orthogonal pure spectra to obtain preprocessed spectra; and
    obtaining, by a regression block, a blood glucose concentration from the preprocessed spectra,
    wherein the obtaining the orthogonal pure spectra comprises:
        obtaining, by a pre-data whitening unit, data whitened NIR spectra based on performing transformation on the human NIR spectra;
        calculating, by an iterative processing unit, an orthogonal pure spectrum from the data whitened NIR spectra;
        calculating new deflated NIR spectra to be transmitted to the iterative processing unit, to compute a new orthogonal pure spectrum based on removal of an effect of the previously calculated orthogonal pure spectrum; and
        combining one or more computed orthogonal pure spectrums to obtain the orthogonal pure spectra.

2. The method as claimed in claim 1, wherein the obtaining the data whitened NIR spectra comprises:
    calculating Eigen vectors of the human NIR spectra using a singular value decomposition; and
    applying a whitening transformation using the Eigen vectors on the human NIR spectra to obtain the data whitened NIR spectra.

3. The method as claimed in claim 2, wherein the calculating the orthogonal pure spectrum comprises:
    computing, by a single processing unit, an estimate spectrum, based on the data whitened NIR spectra and a residual error; and
    reiterating the computing of the estimate spectrum until convergence of learning parameters is achieved to obtain the orthogonal pure spectrum.

4. The method as claimed in claim 3, wherein the computing the estimate spectrum comprises:
    randomly initializing the learning parameters, the learning parameters comprising a weight vector and a bias vector;
    obtaining the estimate spectrum based on the weight vector and the bias vector; and
    computing source statistics for the estimate spectrum, the source statistics comprising Cross correlation and Covariance matrices.

5. The method as claimed in claim 4, wherein the reiterating comprises:
    calculating updated values of the weight vector and the bias vector based on the source statistics of the estimate spectrum;
    calculating an updated estimate spectrum based on the updated values of the weight vector and the bias vector;

determining the updated estimate spectrum as the orthogonal pure spectrum in response to the convergence being achieved for the weight vector; and reiterating the computing of the estimate spectrum in response to the convergence not being achieved for the weight vector.

6. The method as claimed in claim 1, wherein the calculating the new deflated NIR spectra comprises:

deflating the data whitened NIR spectra based on the orthogonal pure spectrum obtained from the iterative processing unit;

determining whether a certain number of orthogonal pure spectrums are obtained; and transmitting the deflated NIR spectra to the iterative processing unit to obtain the new orthogonal pure spectrum in response to the certain number of the orthogonal pure spectrums are not obtained.

7. The method as claimed in claim 1, wherein the obtaining the preprocessed spectra comprises:

performing an extended multiplicative scatter correction (EMSC) method on the human NIR spectra and the orthogonal pure spectra;

performing, by using a Fast Fourier Transform (FFT) block, a filtering method on the human NIR spectra, on which the EMSC method has been performed, to obtain filtered spectra; and performing, on the filtered spectra, drift removal to obtain the preprocessed spectra.

8. The method as claimed in claim 7, wherein the performing the filtering method comprises:

performing a Fourier domain filtering on the human NIR spectra on which the EMSC method has been performed to reduce noise on the human NIR spectra by using a Hanning Window; and removing drift by differentiating, with respect to a wavelength, Fourier domain filtered spectra, to obtain the filtered spectra.

9. The method as claimed in claim 1, wherein the obtaining the blood glucose concentration comprises:

extracting, by a feature extraction block, one or more features from the preprocessed spectra;

obtaining a training data set and a validation data set from the one or more features; and obtaining the blood glucose concentration by performing regression on the training data set and the validation data set.

10. A system for obtaining blood glucose concentration using near infrared spectroscopy (NIR) data, the system comprising:

at least one processor comprising:

an independent component analysis (ICA) temporal module configured to obtain orthogonal pure spectra from human NIR spectra;

a processing module configured to perform one or more preprocessings and drift removal on the human NIR spectra and the orthogonal pure spectra to obtain preprocessed spectra; and a regression block configured to obtain a blood glucose concentration from the preprocessed spectra, wherein the ICA temporal module comprises:

a pre-data whitening unit configured to:

obtain data whitened NIR spectra based on performing transformation on the human NIR spectra;

an iterative processing unit configured to calculate an orthogonal pure spectrum from the data whitened NIR spectra;

a deflation module configured to calculate new deflated NIR spectra to be transmitted to the iterative processing unit, to compute a new orthogonal pure spectrum based on removal of an effect of the previously calculated orthogonal pure spectrum; and a learning algorithm unit configured to combine one or more computed orthogonal pure spectrums to obtain the orthogonal pure spectra.

11. The system of claim 10, wherein the pre-data whitening unit is further configured to:

obtain Eigen vectors of the human NIR spectra using a singular value decomposition; and apply a whitening transformation using the Eigen vectors on the human NIR spectra to obtain the data whitened NIR spectra.

12. The system of claim 11, wherein the learning algorithm unit is configured to:

compute, by a single processing unit included in the learning algorithm unit, an estimate spectrum, based on the data whitened NIR spectra and a residual error.

13. The system of claim 12, wherein the learning algorithm unit is configured to compute the estimate spectrum by performing:

randomly initializing learning parameters, the learning parameters comprising a weight vector and a bias vector;

obtaining the estimate spectrum based on the weight vector and the bias vector; and computing a source statistics for the estimate spectrum, the source statistics comprising Cross correlation and Covariance matrices; and reiterating computing of the estimate spectrum until convergence of the learning parameters is achieved to obtain the orthogonal pure spectrum.

14. The system of claim 13, wherein the reiterating comprises:

calculating updated values of the weight vector and the bias vector based on the source statistics of the estimate spectrum;

calculating an updated estimate spectrum based on the updated values of the weight vector and the bias vector;

determining the updated estimate spectrum as the orthogonal pure spectrum in response to the convergence being achieved for the weight vector; and reiterating the updated values of the weight vector and the bias vector to the single processing unit in response to the convergence not being achieved for the weight vector.

15. The system of claim 10, wherein the deflation module is further configured to:

deflate the data whitened NIR spectra based on the orthogonal pure spectrum obtained from the iterative processing unit;

determine whether a certain number of orthogonal pure spectrums are obtained; and transmit the deflated NIR spectra to the iterative processing unit to obtain the new orthogonal pure spectrum in response to the certain number of the orthogonal pure spectrums not being obtained.

16. The system of claim 10, wherein the processing module comprises:

an extended multiplicative scatter correction (EMSC) module configured to perform an extended multiplicative scatter correction (EMSC) method on the human NIR spectra and the orthogonal pure spectra;

a Fast Fourier Transform (FFT) block configured to perform a filtering method on the human NIR spectra, on which the EMSC method has been performed, to obtain filtered spectra; and a drift removal module configured to perform drift removal on the filtered spectra to obtain the preprocessed spectra.

17. The system of claim 10, wherein the regression block further comprises:

a feature extraction block configured to extract one or more features from the preprocessed spectra;

a separation block configured to obtain a training data set and a validation data set from the one or more features; and a regression model identifier block configured to obtain the blood glucose concentration based on performing regression on the training data set and the validation data set.

* * * * *